(12) United States Patent
Chauve et al.

(10) Patent No.: US 11,060,118 B2
(45) Date of Patent: Jul. 13, 2021

(54) PRODUCTION OF VANILLIN BY FERMENTATION

(71) Applicant: RHODIA OPERATIONS, Paris (FR)

(72) Inventors: Marie Chauve, Lyons (FR); Stéphanie Foucher, Shanghai (CN); Sophie Galinat, Lyons (FR); Guillaume Pireau, Rosny sur Seine (FR)

(73) Assignee: RHODIA OPERATIONS, Aubervilliers (FR)

( * ) Notice: Subject to any disclaimer, the term of this patent is extended or adjusted under 35 U.S.C. 154(b) by 21 days.

(21) Appl. No.: 15/751,058

(22) PCT Filed: Jul. 28, 2016

(86) PCT No.: PCT/EP2016/067997
§ 371 (c)(1),
(2) Date: Feb. 7, 2018

(87) PCT Pub. No.: WO2017/025339
PCT Pub. Date: Feb. 16, 2017

(65) Prior Publication Data
US 2018/0230500 A1   Aug. 16, 2018

(30) Foreign Application Priority Data
Aug. 7, 2015  (EP) .................................... 15306279

(51) Int. Cl.
| C12P 7/24 | (2006.01) |
| C12N 1/20 | (2006.01) |
| C12M 1/00 | (2006.01) |
| C12P 7/22 | (2006.01) |

(52) U.S. Cl.
CPC ............... *C12P 7/24* (2013.01); *C12M 29/04* (2013.01); *C12M 29/18* (2013.01); *C12M 47/10* (2013.01); *C12N 1/20* (2013.01); *C12P 7/22* (2013.01); *Y02P 20/582* (2015.11)

(58) Field of Classification Search
CPC ....................................................... C12P 7/24
See application file for complete search history.

(56) References Cited

FOREIGN PATENT DOCUMENTS

| EP | 1734128 A1 | 12/2006 |
| JP | S61-088872 A | 5/1986 |
| JP | H11-069990 A | 3/1999 |
| JP | 2004-267131 A | 9/2004 |

(Continued)

OTHER PUBLICATIONS

Sciubba. Membrane-based solvent extraction of vanillin in hollow fiber contactors. Desalination 241 (2009) 357-364.*

(Continued)

*Primary Examiner* — Yong D Pak
(74) *Attorney, Agent, or Firm* — Osha Bergman Watanabe & Burton LLP

(57) ABSTRACT

The present invention relates to a new process of vanillin production from a substrate by bioconversion and that allows a continuously producing and removing vanillin from the fermentation broth as it is formed. In particular, the invented process advantageously allows to reduce the residence time of vanillin in the fermenter and to maintain the vanillin concentration, in the fermentation broth, below its toxic level for the microorganism.

18 Claims, 3 Drawing Sheets

(56) References Cited

FOREIGN PATENT DOCUMENTS

WO          0 885 968    * 12/1998
WO    WO 2014/045299    * 3/2014

OTHER PUBLICATIONS

Biotechnological and molecular Approaches for Vanillin Production: A review, Appl. Biochem. Biotech, 2013, 169, 4. Baljinder K., Chakrabprty D.
Process intensification in lactic acid production: A review of membrane based processes, Chem. Eng. Proc, 2009, 48, 1549-1559, Pal P., Sikder J., Roy S., Giorno L.
Office Action issued in Japanese Application No. 2018-506264, dated Mar. 31, 2020 (15 pages).

* cited by examiner

PRODUCTION OF VANILLIN BY FERMENTATION

CROSS-REFERENCE TO RELATED APPLICATIONS

The present application is a U.S. national stage entry under 35 U.S.C. § 371 of International Application No. PCT/EP2016/067997, filed Jul. 28, 2016, which claims priority to International Application No. EP15306279.9 filed on Aug. 7, 2015, the entire content of these applications being incorporated herein by reference for all purposes.

FIELD OF THE INVENTION

The invention relates to a process of vanillin production from a substrate by bioconversion.

BACKGROUND OF THE INVENTION

Vanillin, of chemical name 4-hydroxy-3-methoxybenzaldehyde, is one of the most important aromatic flavor compounds used in foods, beverages, fragrances, pharmaceuticals and polymers. Vanillin was historically extracted from *Vanilla planifolia, Vanilla tahitiensis* and *Vanilla pompona* pods. The demand getting higher today, less than 5% of worldwide vanillin production comes from natural *vanilla* pods. Currently, chemical synthesis is the most important process for producing vanillin.

However, the chemical synthesis, while suitable for the manufacture of perfumes and cosmetics, may give rise to legislative problems in the agri-foodstuffs industries. In addition, synthetic flavourings tend, moreover, to be less well liked by consumers than flavourings of natural origin.

Accordingly, an effort is being made to obtain vanillin produced by means of biotechnological processes which employ microorganisms.

These processes are based on the conversion of following substrates: lignin, phenolic stilbenes, isoeugenol, eugenol, ferulic acid, sugars, vanillic acid, phenolic stilbenes, waste residues and aromatic amino acids under the catalysis of a convenient microorganism like for example *Bacillus, Streptomyces, Pseudomonas* and *Serratia*. The recent review from Kaur and Chakraborty (Kaur B, Chakraborty D. "*Biotechnological and molecular approaches for vanillin production: a review.*" Appl Biochem Biotechnol. 2013 February; 169(4):1353-72) list several biosynthetic pathways and appropriate cells used for bioconversion of vanilloids. The patent application EP 1 734 128 also disclose a method for the production of vanillin by fermentation and biotransformation.

However, the productivity of most bioconversions and fermentations is often limited by the toxicity of products on microorganisms. In particular, most of the already known processes using a biotechnological route for producing vanillin suffer from the vanillin toxicity on microorganisms and degradation. In addition, the vanillin yield is affected by the further transformation of vanillin to degradation products like vanillin alcohol and vanillic acid.

A current challenge in the industry is thus to overcome these inhibitions to improve yield and selectivity.

In this purpose, it was already proposed to couple an extraction process to a bioconversion step.

Thus, a conventional coupling process scheme for biovanillin involves generally the following parts:

- a biotransformation part, generally a fermenter, where microorganisms are synthetizing vanillin and most often byproducts from a substrate,
- a biomass filtration part where the cells are physically separated from a filtrate containing the synthetised products and the residual substrate and then recycled in the fermenter and
- a selective separation part where the target product like the vanillin, is extracted from the other ones which are recycled in the fermenter.

As representative of some separation techniques already considered with a classic fermentation process, may be in particular cited liquid-liquid extraction, membrane-based solvent extraction (MBSE) and adsorption on resins (or on Solvent Impregnated Resins).

However, coupling the bioconversion step to a subsequent extraction process does not solve totally the problem of the toxicity of the vanillin on the microorganism because vanillin is still present in high amount in the fermenter.

Accordingly, the purpose of the present invention is to propose a process allowing to reduce the vanillin concentration in the broth of fermentation in order to limit its inhibition on the microorganism and then to push the bioconversion of the substrate further for increasing the productivity and selectivity for vanillin production.

SUMMARY OF THE INVENTION

More precisely, the invention is directed to a process for producing vanillin by bioconversion from a substrate and in particular ferulic acid, which process comprises at least the steps consisting of cultivating in a fermenter at least one microorganism able to form vanillin by bioconversion of a substrate, feeding said fermenter with at least one substrate to be converted by said microorganism, and recovering from the fermentation broth of said fermenter the so-produced vanillin, wherein said substrate is at least in part added continuously to the fermentation broth of the fermenter, and during the continuous adding of said substrate, a stream of the fermentation broth is continuously extracted from the fermenter through a separating device whereby are provided (i) a fermentation broth composition (a) devoid from said microorganism and (ii) a fermentation broth composition (b) comprising said microorganism with said vanillin being recovered from all or a part of composition (a) and composition (b) being all or at least in part recycled in the fermenter.

Thus, the inventors discovered a novel approach convenient for continuously producing and removing vanillin from the fermentation broth as it is formed. In particular, the invented process advantageously allows to reduce the residence time of vanillin in the fermenter and to maintain the vanillin concentration, in the fermentation broth, below its toxic level for the microorganism.

Furthermore, the continuous feeding of the fermenter with fresh substrate allows to stimulate the bioconversion by bringing more substrate to be converted.

The process according to the invention, with continuous addition of substrate, continuous extraction of broth and recycling of all or part of the fermentation broth composition (b) comprising said microorganism, implies a continuous modification of the content of the fermentation broth. Said modification may have unpredictable consequences on the metabolism of the microorganism. The metabolic scheme of microorganisms producing vanillin is complicated. Therefore, the improvement of the bioconversion to vanillin observed with the process according to the invention could not have been presumed.

According to a preferred embodiment, a first load of substrate is added in the fermenter and, subsequently or simultaneously, some substrate is continuously fed in the fermentation broth in the fermenter.

According to another preferred embodiment, the composition (b) is in totality fed back into the fermenter.

According to another preferred embodiment, the fermentation broth is extracted through a membrane filtration device as separating device whereby are provided (i) a filtrate devoid from said microorganism and (ii) a retentate (b) comprising said microorganism.

According to a specific embodiment, the separating device is only dedicated to form a fermentation broth composition (a) devoid from said microorganism. The so-formed composition (a) is based on vanillin, non-converted substrate and impurities like vanillic acid, vanillyl alcohol, and guaiacol.

In this variant, the invented process involves a supplemental separation technique allowing a selective recovery of vanillin from the composition (a). In particular, the separating device, advantageously a filtration device, may be coupled to a supplemental separating device allowing this selective recovery of vanillin from the composition (a).

For example, the composition (a) may be collected in a tank where the vanillin may be extracted by a liquid-liquid extraction. The FIG. 1 illustrates this embodiment.

The vanillin contained in the composition (a) may be also selectively adsorbed on an adsorbent like a resin. This adsorbent material is subsequently treated to recover and purify vanillin, generally by using an extraction solvent for vanillin. The FIG. 2 illustrates such an embodiment.

In both case, the composition containing the non-converted substrate may be, all or in part, advantageously recycled in the fermenter.

According to another particular embodiment, the separating device allows a simultaneous selective extraction of the vanillin. The FIG. 3 illustrates this embodiment.

In the invented process, only one fermenter is generally used. However, as can be easily understood by the skilled person, the process can also be easily operated with several fermenters, which are then often put in a parallel configuration. When several fermenters are used, they may be substantially identical or identical to each other; besides, the fermenters may work substantially or exactly in the same manner.

DETAILED DESCRIPTION OF THE INVENTION

Fermentation Broth

Figure 1:
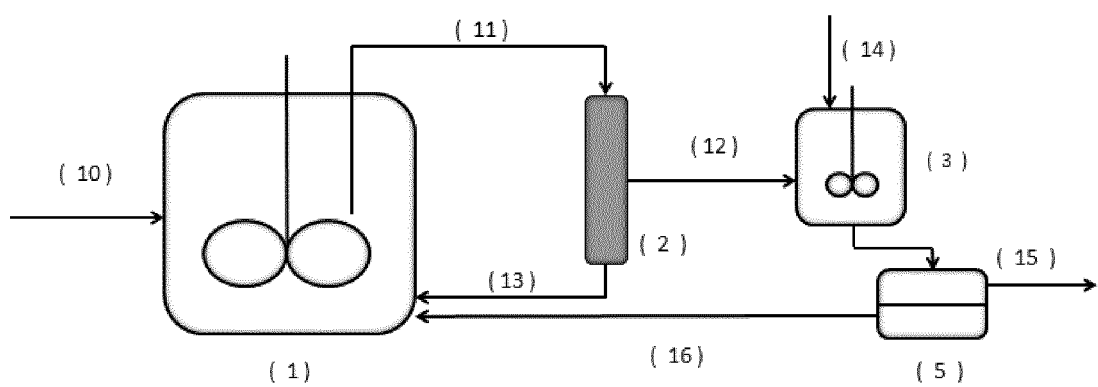
FIG. 1 illustrates an example of process of the invention coupling to the separating device, a liquid-liquid extraction device.

As stated previously the process of the invention, involves the preliminary step of cultivating in a fermenter, at least one microorganism able to convert a substrate in vanillin.

According to the invention the term 'cultivating' is used to denote the growth of microorganism in an appropriate medium.

The term "appropriate medium" designates a medium (e.g., a sterile, liquid media) comprising nutrients essential or beneficial to the maintenance and/or growth of the cell such as carbon sources or carbon substrates, nitrogen sources, urea, ammonium sulfate, ammonium chloride, ammonium nitrate and ammonium phosphate; phosphorus sources; metal salts, for example magnesium salts, cobalt salts and/or manganese salts; as well as growth factors such as amino acids and vitamins. Typical medium is composed of 10 g/l of yeast extract, 20 g/l of peptone and 20 g/l of carbon source.

The term "source of carbon" according to the present invention denotes any source of carbon that can be used by those skilled in the art to support the normal growth of a yeast. Yeasts use sugars as their main carbon and energy source, but non-conventional carbon sources can be accepted too.

The source of carbon may be selected among the group consisting of glucose, fructose, mannose, xylose, arabinose, galactose, lactose, ethanol, cellobiose, glycerol and polysaccharides such as cellulose, and mixtures thereof.

An especially preferred source of carbon is ethanol and/or glucose. Examples of suitable nitrogen sources are inorganic nitrogen sources such as nitrates and ammonium salts and organic nitrogen sources such as yeast extract, soya bean meal, cotton seed meal, casein, casein hydrolysate, wheat gluten and corn steep liquor.

Inorganic salts which can be used are, for example, inter alia, sulphates, nitrates, chlorides, carbonates and phosphates of sodium, potassium, magnesium, calcium, zinc and iron.

The cultivation step is performed under controlled conditions of pH, temperature, $pO_2$ and aeration, conditions well known to a person skilled in the art.

The culture temperature is preferably in the range from 10 to 55° C., particularly preferably in the range from 30 to 45° C. The pH of the medium is preferably 3 to 9, in particular 4 to 8.

The microorganism may be any microorganism able to form vanillin by bioconversion of a convenient substrate.

As convenient microorganisms may be in particular cited the microorganisms selected in the group consisting of *Bacillus, Streptomyces, Pseudomonas* and *Serratia* and preferably is *Streptomyces setonii* and more preferably the strain ATCC 39116.

Substrate

As already stated previously, several types of carbon substrate may be considered.

More particularly, the substrate is selected among the group consisting of sugars (like glucose, fructose, mannose, xylose, arabinose, galactose and lactose, with a preference being given to glucose), ferulic acid, vanillic acid, phenylalanine, eugenol and mixtures thereof.

More preferably, the substrate is ferulic acid.

According to the invented process, at least a part of this substrate is continuously added to the fermenter.

This means that the continuous feeding of substrate may not constitute the only route of adding.

Thus, according to a specific embodiment, a first load of substrate may be added to the fermentation broth and subsequently or simultaneously some substrate, generally under the form of a solution, is continuously added to the fermentation broth in the fermenter.

More precisely, the first load of substrate is added in the fermenter and the bioconversion is let promoted in batch for ensuring a good enzymatic activity. Then a fresh solution of substrate is continuously loaded in the fermenter.

As previously stated, the invented process involves that, simultaneously to the continuous feeding of the substrate, a stream of fermentation broth is extracted through a separating device whereby are provided (i) a fermentation broth composition (a) devoid from said microorganism and (ii) a fermentation broth composition (b) comprising said microorganism.

This continuous extraction of some fermentation broth, simultaneously to the continuous feeding of substrate, allows to maintain a constant volume of fermentation broth in the fermenter and to limit efficiently the residence time of vanillin in the fermenter with the advantages detailed hereabove.

Advantageously, the residence time in the fermenter ranges from 1 to 24 hours and preferably from 3 to 10 hours. Thus, the respective flow rates of feeding of substrate, $Q_{feed}$, and of the stream of composition (a), $Q_{(a)}$, may be adjusted to reduce the residence time of the fermenter.

$Q_{(a)}$ and $Q_{feed}$ may have advantageously closed values and in particular are equal.

By definition the residence time is as short as the flow rate is high.

$$t_r = \frac{V}{Q} \quad (1)$$

with: $t_r$ is the residence time in h
V is the fermenter working volume in L
$Q=Q_{(a)}=Q_{feed}$ the flow rate in L/h The flow rates of feeding of substrate, $Q_{feed}$, and of the stream of composition (a), $Q_{(a)}$, are also advantageously adjusted for keeping a constant volume of the fermentation broth in the fermenter.

To maintain the flow rate of $Q_{feed}$ equal to the flow rate of composition (a) $Q_{(a)}$ it may be advantageous to use three pumps, one for the feeding of the substrate stream in the fermenter, another for the continuous extracting of some fermentation broth from the fermenter and another on the composition (a) line.

The substrate is preferably fed under the form of an aqueous solution having preferably a pH ranging from 8 to 9. This aqueous solution may also contain nutritive components for the fermentation broth of said fermenter. In particular, it may consist in a complete medium with salts and nutrient supplemented with the substrate.

According to preferred embodiment, the concentration of the substrate and in particular of ferulic acid ranges from 5 to 60 g/L in the fermentation broth.

Separating Device

As already submitted here-above, it is proceed through the separating device to a continuous extraction of some broth fermentation and thus to a continuous formation of (i) a fermentation broth composition (a) devoid from said microorganism and (ii) a fermentation broth composition (b), this last one being at least in part recycled in the fermenter.

Any device allowing the separation of said compositions may be used in the present invention. Preferably, the separating device is a filtration membrane device. Such a filtration device allows to recover from the extracted fermentation broth, a retentate containing the microorganism and a filtrate free from microorganism.

According to a first embodiment, the separating device allows a simultaneous selective extraction of vanillin from the extracted fermentation broth.

Such a separating device may advantageously be a filtration membrane device based on a Membrane Base Solvent Extraction (MBSE). The convenient membranes for the present invention are hydrophobic membranes and in particular a PTFE membrane.

The solution of non-converted substrate recovered from the selective separating device may be, all or in part, recycled in the fermenter.

Figure 3:
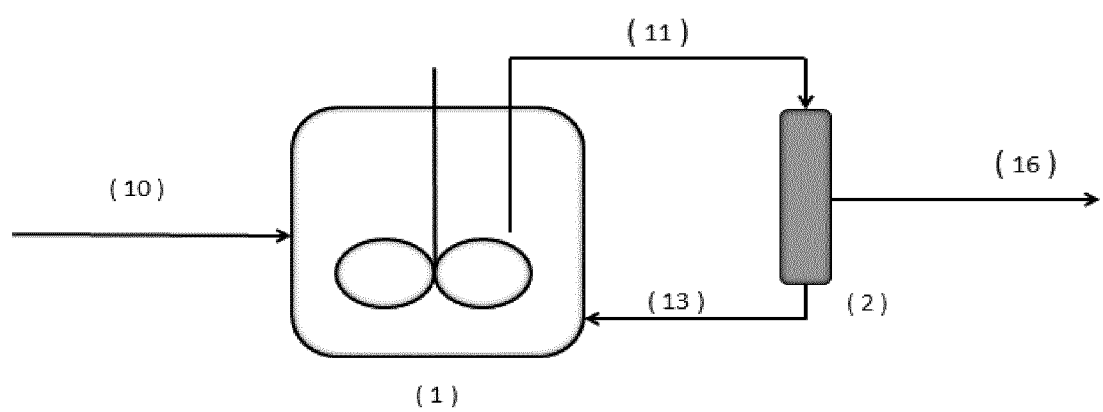
FIG. 3 illustrates another example of process of the invention using as separating device, a filtration device based on a selective membrane for vanillin.

This specific embodiment is schematized on FIG. 3.

According to another embodiment, the separating device does not allow to extract selectively the vanillin form the fermentation broth. Thus, it may be the case of a filtration device based on a membrane only exhibiting a selectivity with respect to microorganisms. Consequently, the separating device forms a composition (a) containing non-converted substrate and bioconversion products.

In such a case, the invented process involves a subsequent and supplemental separation technique for extracting of vanillin from this composition (a).

This supplemental separation technique may be any conventional methods useful for performing the expected extraction of vanillin.

According to a first embodiment, it may be a liquid-liquid extraction.

The extraction solvent for the vanillin may be selected among the extraction solvents known by the person skilled in the art. In particular, it may be selected form the group consisting of alcohols, alkyl acetate, hexane and mixtures thereof, and is preferably N-isobutyl acetate.

Regarding this specific embodiment, reference may be made to the content of WO 2015/011112 and EP0885968. This specific embodiment of the invented process is illustrated on FIG. 1.

According to a second embodiment, it may be a separation technique based on selective adsorption of the vanillin on the resin of an adsorption column.

Such adsorber resins like for example polystyrenic or polyphenolic resins are known from the man skilled in the art.

It can be adsorber resins such as Amberlite XAD-2, Amberlite XAD-7, XAD-16, Lewatit OC 1062 or OC 1064 (cited in U.S. Pat. No. 6,133,003). The vanillin is subsequently extracted from such a resin with a convenient extraction solvent. A specific embodiment of such a process is illustrated on FIG. 2.

Whatever the type of supplemental separating device, the composition free of vanillin and containing non-converted substrate, that is also recovered through this supplemental separation technique may be at least in part recycled in the fermenter.

Vanillin obtained by the process according to the invention may be used as such or may be further purified. Typical purification step may consist in an extraction with a solvent, a distillation, a crystallization, or in a combination of said purification steps, for instance an extraction or a distillation followed by a crystallization.

Figure 2:
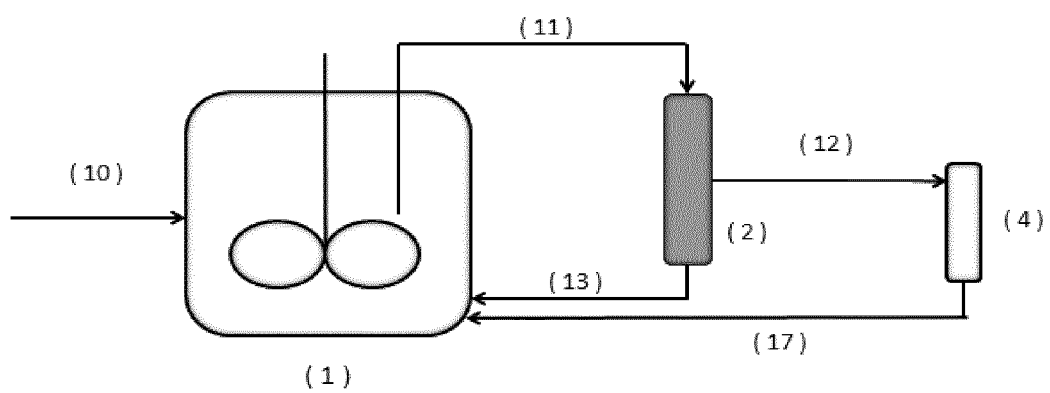
FIG. 2 illustrates another example of process of the invention coupling to the separating device, an adsorption column.

The FIGS. 1 to 3, illustrate specific embodiments of the invented process. A fermenter (1) containing a fermentation medium, the microorganism and preferably some substrate, is continuously feed with a solution of substrate (10) at a controlled flow rate $Q_{feed}$. Some fermentation broth (11) is continuously circulated from the fermenter to a separating device (2) whereby are provided a stream of fermentation broth composition (a) devoid from said microorganism (12) or (16) with a controlled flow rate $Q_{(a)}$ and (ii) a stream of fermentation broth composition (b) (13) comprising said microorganism that is recycled back into the fermenter (1).

On FIGS. 1 and 2, the composition (a) is circulated from the separating device (2) to a supplemental separating device (3) or (4).

On FIG. 1, the separating device is an extraction device (3) that is fed with at least one extraction solvent (14) and the composition (a) (12). The liquid-liquid extraction is conducted into the extraction device and the content of the device is then directed to a holding tank (5) to allow for phase separation by decanting. The extractant solution (15) containing vanillin is collected and the other solution (16) is recycled back to the fermenter.

On FIG. 2, the separating device is an adsorption column (4) for vanillin. The composition (a) (12) is circulated through the adsorption column and a composition free of vanillin (17) is recovered at the end of the adsorption column and pumped back to the fermenter. The vanillin is further extracted from the adsorption column.

On FIG. 3, the separating device (2) is a filtration device based on a Membrane Base Solvent Extraction (MBSE). The extracted fermentation broth (11) is circulated through the membrane of said device to provide a composition free of vanillin (13) that is pumped back to the fermenter and a composition containing vanillin (16).

A better understanding of the present invention will be gained from the additional description which follows, which refers to examples of implementation of the process according to the invention.

It should, however, be clearly understood that these examples are given only by way of illustration of the subject of the invention, of which they in no way constitute a limitation.

EXAMPLES

Example 1

500 mL shake flask containing 0.1 g of $KH_2PO_4$, 0.4 g of $Na_2HPO_4$, $12H_2O$, 1 g of yeast extract, 0.02 g of $MgSO_4$, $7H_2O$, 10 g of a solution containing 2 g of glucose in 38 g of water is inoculated with 1 mL of the strain *Streptomyces setonii* ATCC 39116 and cultivated at 37° C., 150 rpm, for 24 h.

A fermenter of 2 L (total volume) containing 12 g of yeast extract, 1.2 g of $MgSO_4$, $7H_2O$, 48 g of glucose and 1391 g of water is inoculated with 50 mL of the preculture prepared in the shake flask. The strain is cultured under fermentation conditions at 37° C., 1000 rpm (Rushton turbine), with an aeration of 0.67 vvm at atmospheric pressure for around 24 h. Initial pH is 7 and it is let free during this growth phase. The biomass could reach up between 8 and 10 g/L (dry weight).

Example 2

*Streptomyces setonii* was cultivated according to Example 1.

300 mL of the solution is removed from the fermenter. pH is increased at 8.3 and maintained constant, aeration is decreased at 0.47 vvm and dissolved oxygen is maintained constant at 30% changing agitation rate. Temperature and pressure do not change.

A solution containing 24 g of ferulic acid, 16 g of NaOH (30%) and 240 g of water is added in the fermenter.

After 6 h, a solution containing 35 g/L of ferulic acid is fed continuously at 0.159 L/h. In parallel, the fermentation media is filtrate using the microfiltration module type plan RAYFLOW 100 (Orelis) equipped with a PVDF membrane (Cut-off=0.15 μm). The total surface in the membrane is 0.2 $m^2$, inlet pressure is around 1.5 bar and outlet pressure is around 1 bar.

The filter is feeding with a flow of 133.4 L/h. In these conditions, the filtrate flow is 1.9 L/h and the retentate flow is 131.5 L/h. The filtration was performed during 24 h and the lower measured filtrate flow is 1.1 L/h. At any time, the filtrate was free of microorganism.

The retentate is reintroduced in the fermenter and 0.160 L/h of the filtrate is removed (the other part of the filtrate is reintroduced in the fermenter). This continuous process is performed during 39 hours. Samples are regularly taken and analyzed by HPLC.

At the end, 0.52 mol of ferulic acid was consumed and 0.24 mol of vanillin was produced and 0.47 mol of total products (vanillin, vanillic acid, vanillic alcohol and gaiacol) were produced.

The maximum vanillin concentration in the fermenter is observed after 25.5 h of bioconversion and is 10.6 g/L.

Example 3

*Streptomyces setonii* was cultivated according to Example 1.

300 mL of the solution is removed from the fermenter. pH is increased at 8.3 and maintained constant, aeration is decreased at 0.47 vvm and dissolved oxygen is maintained constant at 30% changing agitation rate. Temperature and pressure do not change.

A solution containing 24 g of ferulic acid, 16 g of NaOH (30%) and 240 g of water is added in the fermenter.

After 6 h, a solution containing 28 g/L of ferulic acid is fed continuously at 0.27 L/h. In parallel, the fermentation media is filtrate using the microfiltration module described in Example 2. The retentate is reintroduced in the fermenter and 0.27 L/h of the filtrate is removed (the other part of the filtrate is reintroduced in the fermenter). This continuous process is performed during 44 hours. Samples are regularly taken and analyzed by HPLC.

At the end, 1.03 mol of ferulic acid was consumed and 0.42 mol of vanillin was produced and 0.89 mol of total products (vanillin, vanillic acid, vanillic alcohol and gaiacol) were produced.

The maximum vanillin concentration in the fermenter is observed after 24.5 h of bioconversion and is 8.9 g/L.

The invention claimed is:
1. A process for producing vanillin by bioconversion, comprising:
  cultivating in a fermenter at least one microorganism able to form vanillin by bioconversion of at least one substrate, feeding said fermenter with the at least one substrate to be converted into vanillin by said microorganism, feeding said fermenter with a fresh culture medium comprising a carbon source and/or a nitrogen source and a metal salt selected from the group consisting of manganese, cobalt, or magnesium salt, and recovering vanillin from the fermentation broth of said fermenter, wherein:

said at least one substrate is at least in part added continuously to the fermentation broth of the fermenter in a solution also containing nutritive components for the fermentation broth of said fermenter, and during the continuous adding of said substrate, a stream of the fermentation broth is continuously extracted from the fermenter through a separating device to provide:

(i) a fermentation broth composition (a) that is devoid from said microorganism, and (ii) a fermentation broth composition (b) that comprises said microorganism, wherein the vanillin is recovered from all or a part of composition (a) and composition (b) is, all or at least in part, recycled in the fermenter, wherein a concentration of the at least one substrate ranges from 5 to 60 g/L in the fermentation broth, wherein the microorganism is selected from the group consisting of *Bacillus, Streptomyces, Pseudomonas* and *Serratia*.

2. The process of claim 1, wherein a first load of substrate is added in the fermenter and, subsequently or simultaneously, some substrate is continuously added to the fermentation broth in the fermenter.

3. The process according to claim 1, wherein the residence time of the fermenter ranges from 1 to 24 hours.

4. The process according to claim 1, wherein the flow rates of feeding of substrate, and of the stream of composition (a) are adjusted for keeping a constant volume of the fermentation broth in said fermenter.

5. The process according to claim 1, wherein said at least one substrate is ferulic acid.

6. The process according to claim 1, wherein the at least one substrate is fed in continuously under the form of a solution having a pH ranging from 7 to 9.

7. The process according to claim 1, wherein the separating device also allows a simultaneous selective extraction of vanillin.

8. The process according to claim 7, wherein said separating device is a filtration membrane device based on a Membrane Base Solvent Extraction.

9. The process according to claim 1, wherein the separating device forms a composition (a) containing non-converted substrate and bioconversion products.

10. The process according to claim 9, involving a subsequent and supplemental separation technique that allows a selective recovery of vanillin from composition (a).

11. The process according to claim 10, wherein the supplemental separation technique is based on a selective adsorption of vanillin on the resin of an adsorption column.

12. The process according to claim 10, wherein the supplemental separation technique is based on a liquid-liquid extraction.

13. The process according to claim 10, wherein the supplemental separation technique allows the recovery of a composition free of vanillin and containing non-converted substrate, and wherein said composition free of vanillin and containing non-converted substrate is at least in part recycled in the fermenter.

14. The process according to claim 1, further comprising a purification step or a combination of purification steps of said recovered vanillin.

15. The process according to claim 3, wherein the residence time of the fermenter ranges from 3 to 10 hours.

16. The process according to claim 1, wherein the microorganism is *Streptomyces setonii*.

17. A process for producing vanillin by bioconversion from a substrate, which process comprises at least the steps consisting of:

cultivating in a fermenter at least one microorganism able to form vanillin by bioconversion of a substrate, feeding said fermenter with at least one substrate to be converted by said microorganism, feeding said fermenter with a fresh culture medium comprising a carbon source and/or a nitrogen source and a metal salt selected from the group consisting of manganese, cobalt, or magnesium salt and recovering from the fermentation broth of said fermenter the so-produced vanillin, wherein:

said substrate is at least in part added continuously to the fermentation broth of the fermenter in a solution also containing nutritive components for the fermentation broth of said fermenter, and during the continuous adding of said substrate, a stream of the fermentation broth is continuously extracted from the fermenter through a separating device whereby are provided:

(i) a fermentation broth composition (a) devoid from said microorganism, and (ii) a fermentation broth composition (b) comprising said microorganism, with said vanillin being recovered from all or a part of composition (a) and composition (b) is, all or at least in part, recycled in the fermenter, wherein said substrate is ferulic acid.

18. A process for producing vanillin by bioconversion from a substrate, which process comprises at least the steps consisting of:

cultivating in a fermenter at least one microorganism able to form vanillin by bioconversion of a substrate, feeding said fermenter with at least one substrate to be converted by said microorganism, feeding said fermenter with a fresh culture medium comprising a carbon source and/or a nitrogen source and a metal salt selected from the group consisting of manganese, cobalt, or magnesium salt and recovering from the fermentation broth of said fermenter the so-produced vanillin, wherein:

said substrate is at least in part added continuously to the fermentation broth of the fermenter in a solution also containing nutritive components for the fermentation broth of said fermenter, and during the continuous adding of said substrate, a stream of the fermentation broth is continuously extracted from the fermenter through a separating device whereby are provided:

(i) a fermentation broth composition (a) devoid from said microorganism, and (ii) a fermentation broth composition (b) comprising said microorganism, with said vanillin being recovered from all or a part of composition (a) and composition (b) is, all or at least in part, recycled in the fermenter, wherein a concentration of the substrate ranges from 5 to 60 g/L in the fermentation broth, and wherein said substrate is ferulic acid.

* * * * *